(12) United States Patent
Overheul et al.

(10) Patent No.: US 8,840,853 B1
(45) Date of Patent: Sep. 23, 2014

(54) INTEGRATED ETHANOL AND BIODIESEL FACILITY

(71) Applicant: WB Technologies LLC, Sedgwick, KS (US)

(72) Inventors: Rachel Overheul, Sedgwick, KS (US); Brandon Awtrey, Sedgwick, KS (US); Daniel Johnson, Sedgwick, KS (US)

(73) Assignee: WB Technologies LLC, Sedgwick, KS (US)

( * ) Notice: Subject to any disclaimer, the term of this patent is extended or adjusted under 35 U.S.C. 154(b) by 0 days.

(21) Appl. No.: 14/243,352

(22) Filed: Apr. 2, 2014

Related U.S. Application Data

(62) Division of application No. 14/168,174, filed on Jan. 30, 2014, now Pat. No. 8,722,924.

(60) Provisional application No. 61/898,828, filed on Nov. 1, 2013.

(51) Int. Cl.
  *B01J 19/00* (2006.01)
  *C11C 3/10* (2006.01)
  *C12P 7/10* (2006.01)

(52) U.S. Cl.
  CPC ... *C12P 7/10* (2013.01); *C01L 1/19* (2013.01); *C11C 3/10* (2013.01)
  USPC ............ 422/600; 422/608; 422/620; 422/630

(58) Field of Classification Search
  None
  See application file for complete search history.

(56) References Cited

U.S. PATENT DOCUMENTS

| | | | |
|---|---|---|---|
| 5,710,030 A | * | 1/1998 | Anderson ..................... 435/134 |
| 6,355,456 B1 | | 3/2002 | Hallberg et al. |
| 6,927,048 B2 | | 8/2005 | Verser et al. |
| 7,263,934 B2 | | 9/2007 | Copeland et al. |
| 7,297,236 B1 | | 11/2007 | Vander Griend |
| 7,321,052 B2 | | 1/2008 | Miller et al. |
| 7,524,418 B2 | | 4/2009 | Hirl |
| 7,544,495 B2 | | 6/2009 | Wilkening et al. |
| 7,572,353 B1 | | 8/2009 | Vander Griend |
| 7,604,743 B2 | | 10/2009 | Hirl |
| 7,608,729 B2 | | 10/2009 | Winsness et al. |

(Continued)

FOREIGN PATENT DOCUMENTS

BR  WO2010/088748 A1  8/2010
WO  WO2007/146971 A1  12/2007

(Continued)

OTHER PUBLICATIONS

Alles et al. "Integrated Corn-Based Biorefinery: A Study in Sustainable Process Development" *Sustainable Development in the Process Industries: Cases and Impact*, Edited by Jan Harmsen and Joseph B. Powell; John Wiley & Sons, Inc.; 2010.

(Continued)

*Primary Examiner* — Jennifer A Leung
(74) *Attorney, Agent, or Firm* — Hovey Williams LLP

(57) ABSTRACT

An integrated facility for the co-production of ethanol and biodiesel fuel is provided. Ethanol and corn oil, the primary product and a by-product from the ethanol plant, are utilized as feedstocks for a biodiesel plant operating within the same general facility as the corn ethanol plant. By-products of the biodiesel plant, principally crude liquid glycerol and gaseous ethanol or methanol, are recycled to various parts of the ethanol plant.

6 Claims, 2 Drawing Sheets

(56) References Cited

U.S. PATENT DOCUMENTS

| | | |
|---|---|---|
| 7,649,086 B2 | 1/2010 | Belanger et al. |
| 7,857,872 B2 | 12/2010 | Krasutsky et al. |
| 7,867,365 B2 | 1/2011 | Brown |
| 7,927,491 B2 | 4/2011 | Kotelko et al. |
| 7,943,791 B2 * | 5/2011 | McNeff .................. 554/174 |
| 7,989,646 B2 | 8/2011 | Bakshi |
| 8,123,822 B2 | 2/2012 | Morgan |
| 8,152,867 B2 | 4/2012 | Dumenil |
| 8,153,850 B2 | 4/2012 | Hall et al. |
| 8,168,037 B2 | 5/2012 | Winsness |
| 8,207,362 B2 | 6/2012 | Morris |
| 8,227,015 B2 | 7/2012 | Bruinsma et al. |
| 8,288,138 B2 | 10/2012 | Birkmire et al. |
| 8,354,564 B2 | 1/2013 | Brown et al. |
| 8,454,802 B2 | 6/2013 | Redford |
| 8,540,880 B1 | 9/2013 | Shah et al. |
| 8,540,881 B1 | 9/2013 | Shah et al. |
| 8,546,627 B2 | 10/2013 | Gruber et al. |
| 2003/0019736 A1 | 1/2003 | Garman |
| 2007/0099278 A1 | 5/2007 | Aare |
| 2007/0117195 A1 | 5/2007 | Warner et al. |
| 2007/0260078 A1 | 11/2007 | Bhat et al. |
| 2008/0176298 A1 | 7/2008 | Randhava et al. |
| 2008/0229653 A1 | 9/2008 | Iversen et al. |
| 2008/0282606 A1 | 11/2008 | Plaza et al. |
| 2009/0017164 A1 | 1/2009 | Shisler et al. |
| 2009/0031615 A1 | 2/2009 | Joshi et al. |
| 2009/0126262 A1 | 5/2009 | Asthana et al. |
| 2009/0148920 A1 | 6/2009 | Schreck |
| 2009/0239185 A1 | 9/2009 | Deline et al. |
| 2009/0288988 A1 | 11/2009 | Mayeur et al. |
| 2009/0311374 A1 | 12/2009 | Beaver et al. |
| 2010/0021980 A1 | 1/2010 | McDonald et al. |
| 2010/0028484 A1 | 2/2010 | Kriesler et al. |
| 2010/0155296 A1 | 6/2010 | Aves et al. |
| 2010/0178675 A1 | 7/2010 | Lawton, Jr. et al. |
| 2010/0221804 A1 | 9/2010 | Veit et al. |
| 2010/0252346 A1 | 10/2010 | Khouw et al. |
| 2010/0260918 A1 | 10/2010 | Wang et al. |
| 2010/0317091 A1 | 12/2010 | Veit et al. |
| 2011/0035993 A1 | 2/2011 | Loescher |
| 2011/0062054 A1 | 3/2011 | Gao et al. |
| 2011/0126448 A1 | 6/2011 | Dumenil |
| 2011/0315541 A1 | 12/2011 | Xu |
| 2012/0048716 A1 | 3/2012 | Sonnek et al. |
| 2012/0051980 A1 | 3/2012 | Gallop et al. |
| 2012/0064213 A1 | 3/2012 | Lee |
| 2012/0142983 A1 | 6/2012 | Vermeiren et al. |
| 2012/0181161 A1 | 7/2012 | Mahler |
| 2012/0205324 A1 | 8/2012 | Cantrell et al. |
| 2012/0240452 A1 | 9/2012 | Erdoes, Jr. et al. |
| 2012/0279111 A1 | 11/2012 | Blasco Garcia |
| 2012/0294977 A1 | 11/2012 | Bruinsma et al. |
| 2012/0301598 A1 | 11/2012 | Karges et al. |
| 2013/0010987 A1 | 1/2013 | Abolfathi et al. |
| 2013/0032175 A1 | 2/2013 | Redford |
| 2013/0130343 A1 | 5/2013 | Purtle et al. |
| 2013/0164795 A1 | 6/2013 | Lowe et al. |
| 2013/0216688 A1 | 8/2013 | Bruinsma et al. |
| 2013/0309738 A1 | 11/2013 | Barr et al. |

FOREIGN PATENT DOCUMENTS

| | | |
|---|---|---|
| WO | WO2011/075671 A2 | 6/2011 |
| WO | WO2012/036857 A2 | 3/2012 |
| WO | WO2012/125739 A1 | 9/2012 |
| WO | WO2012/145230 A1 | 10/2012 |
| WO | WO2013/033369 A2 | 3/2013 |

OTHER PUBLICATIONS

Cardona et al. "Fuel ethanol production: Process design trends and integration opportunities" Bioresource Technology 98 (2007) 2415-2457.

Dien et al. "Fermentation of 'Quick Fiber' Produced from a Modified Corn-Milling Process into Ethanol and Recovery of Corn Fiber Oil" Applied Biochemistry and Biotechnology (2004) vol. 113-116.

Leoneti, et al. "Glycerol as a by-product of biodiesel production in Brazil: Alternatives for the use of unrefined glycerol" Renewable Energy 45 (2012) 138-145.

Moser et al. "Biodiesel from Corn Distillers Dried Grains with Solubles: Preparation, Evaluation, and Properties" Bioenergy Research (Jun. 2012), vol. 5, No. 2, pp. 439-449.

Nigam et al. "Production of liquid biofuels from renewable resources" Progress in Energy and Combustion Science 37 (2011) 52-68.

Shi et al. "Bioresource Technology" Bioresource Technology 128 (2013) 100-106.

Biomass Program: Integrated Corn-Based Bio-Refinery; U.S. Dept of Energy Brochure 2006.

Wang et al. "Effect of the Corn Breaking Method on Oil Distribution between Stillage Phases of Dry-Grind Corn Ethanol Production" J. Agric. Food Chem. 2008, 56, 9975-9980.

Wukovits et al. "Energy self supply of a bio-ethanol production plant by utilisation of renewable energy from residues from feedstock and ethanol production" CHISA 2006—17th International Congress of Chemical and Process Engineering (2006). (Abstract only).

* cited by examiner

INTEGRATED ETHANOL AND BIODIESEL FACILITY

CROSS-REFERENCE TO RELATED APPLICATION

This application is a division of application Ser. No. 14/168,174, filed Jan. 30, 2014, now U.S. Pat. No. 8,722,924, and claims the benefit of provisional application Ser. No. 61/898,828, filed Nov. 1, 2013, and both of these applications are incorporated by reference herein in their entirety.

BACKGROUND OF THE INVENTION

1. Field of the Invention

The present invention generally pertains to an integrated facility for the co-production of ethanol and biodiesel fuel. In particular, corn oil isolated from the whole stillage of a corn ethanol distillation process is utilized as a feedstock for a biodiesel plant, along with alcohol (e.g., methyl alcohol, ethyl alcohol, and mixtures thereof), operating within the same general facility as the corn ethanol plant. By-products of the biodiesel plant, such as liquid crude glycerol and gaseous or liquid alcohols, can be utilized in various parts of the ethanol plant thereby increase the operating efficiency thereof.

2. Description of the Prior Art

Corn oil is a by-product of a corn ethanol production. The corn oil is generally carried through the fermentation and distillation portions of a corn ethanol plant into the whole stillage that is removed from the distillation system. The whole stillage is commonly separated into a thin stillage, which includes the corn oil, and a cake that can be dried to produce dried distillers grains with solubles (DDGS), which can be used as an animal feed. The thin stillage can be processed to remove moisture therefrom and form nutritive syrup that can also be used as an animal feed material. Alternatively, the corn oil may be extracted from the thin stillage and be made a saleable product.

The corn oil extracted from the thin stillage has many industrial uses, such as in soaps, paints, rustproofing materials, inks, textiles, and insecticides. Corn oil can also be used as a feedstock in the production of alternative fuels such as biodiesel and renewable diesel. Biodiesel refers to a vegetable oil- or animal fat-based diesel fuel comprising long-chain alkyl (methyl, ethyl, or propyl) esters. Biodiesel is generally not considered to be a full replacement of conventional petrodiesel for use in most diesel engines. Rather, it is generally blended with petrodiesel for use in the retail diesel fuel marketplace. Renewable diesel, on the other hand, is produced by hydrotreatment of corn oil, for example, resulting in a hydrocarbon fuel that is very similar to petroleum diesel in its chemical composition.

A number of reaction schemes exist for conversion of corn oil into renewable diesel. Hydrotreating is one such process in which the corn oil feedstock is reacted with hydrogen under elevated temperature and pressure to change the chemical composition of the feedstock. In the case of renewable diesel, hydrogen is introduced to the feedstock in the presence of a catalyst convert the triglyceride molecules into paraffinic hydrocarbons. In addition to creating a fuel that is very similar to petrodiesel, this process creates other hydrocarbon by-products including lower hydrocarbon fuel gas compounds (e.g., methane, ethane, propane, and butane) and higher hydrocarbon naphtha.

Production of biodiesel usually involves using corn oil and alcohol as feedstocks to a biodiesel reactor where the corn oil first undergoes an acid esterification reaction whereby the free fatty acids are converted to an alkyl ester through the introduction of a strong acid (e.g., sulfuric acid). The triglycerides are then subjected to a base-catalyzed reaction in the presence of strong base (e.g., KOH) and the alcohol feedstock, in order to form alkyl esters. The ester reaction product is then separated from the glycerol fraction which also contained excess alcohol used in the transesterification reaction.

Generally, the corn oil and/or alcohol feedstocks are produced at a plant location remote from the biodiesel facility, thus requiring transport of these feedstocks via pipeline, railway tankers, or tanker trucks. This added transportation cost increases the overall expense in the manufacture of biodiesel and decreases its competitiveness with petrodiesel as an alternative fuel source.

The following references describe various types of ethanol and biodiesel production methods: U.S. Pat. No. 6,927,048, U.S. Pat. No. 7,608,729, U.S. Pat. No. 7,649,086, U.S. Pat. No. 8,152,867, U.S. Pat. No. 8,227,015, U.S. Pat. No. 8,454,802, US2008/0176298, US2009/0017164, US2009/0311374, US2010/0021980, US2010/0028484, US2010/0178675, US2010/0260918, US2011/0126448, US2012/0051980, US2012/0064213, US2012/0301598, US2013/0032175, US2013/0102045, US2013/0130343, US2013/0164795, WO2007/146971, WO2012036857, WO2012/125739, WO2012/145230, and WO2013033369.

SUMMARY OF THE INVENTION

The present invention overcomes many of the problems outlined above and provides improved processes and plant systems for the co-production of ethanol and biodiesel fuel in combined facilities having both an ethanol plant and a biodiesel plant, wherein the plants are located in close proximity allowing various products and by-products from each plant to be easily transferred to the other plant as desired to increase the efficiency of the overall, dual-plant facility.

In one aspect of the invention, an integrated process or the co-production of ethanol and biodiesel fuel comprises the steps of distilling an ethanol-containing beer within distillation apparatus of an ethanol plant using corn as a feedstock, and producing ethanol and a corn oil product. Thereafter, the corn oil product is directed from the ethanol plant to a proximal biodiesel fuel plant; the corn oil product and an alcohol are used as joint feedstocks in the diesel plant, where the corn oil product and alcohol are reacted to produce a biodiesel fuel and by-products comprising an alcohol, e.g., ethanol and/or methanol, and glycerol. These by-products are then transferred back to the ethanol plant for use therein.

In one embodiment, the transferring step comprises the steps of initially condensing the gaseous alcohol by-product to generate a condensed liquid by-product. This liquid by-product is directed back to the ethanol plant for mixing with the ethanol-containing beer. Alternately, the gaseous alcohol by-product may be combined with the $CO_2$-containing overhead from the beer prior to stripping of the $CO_2$. Still further, this gaseous by-product may be combined with a process steam overhead generated by an evaporation system used to recover the corn oil by-product.

In another aspect of the invention, the liquid crude glycerol generated as a by-product in the diesel fuel plant is directed back to the ethanol mixture with the beer, and/or may be added to a concentrated thin stillage product, which is further processed to generate a syrup.

A still further aspect of the invention involves use of the bottoms of the biodiesel distillation apparatus of the diesel fuel plant. These bottoms, principally comprising high boiling components and unreacted mono-, di-, and triglycerides, can be added to the solids output from the ethanol plant (e.g., a cake), which are normally used to produce animal feeds.

The invention also provides integrated plants for the co-production of ethanol and biodiesel fuel corresponding to the foregoing method aspects of the invention. Thus, such a facility may include an ethanol plant comprising apparatus operable to produce ethanol and a corn oil product from an ethanol-containing beer; and a biodiesel plant comprising a reactor assembly operably coupled with the ethanol plant apparatus to receive at least some of the corn oil product from the ethanol plant, and to react the corn oil product with alcohol to produce biodiesel fuel and outputs such as the gaseous and/or liquid by-product containing alcohol; the liquid crude glycerol; and/or the bottoms from a biodiesel distillation device. Transfer structure(s), typically standard interconnecting transfer pipes or lines, are provided to direct one or more of the biodiesel outputs from the biodiesel plant as desired to the ethanol plant for use therein, in some or all of the ethanol plant locations described previously.

It will be appreciated that the present invention maximizes the efficiencies of both the ethanol and diesel fuel plants forming a part of the overall production facilities contemplated by the invention. Thus, the principal products of the ethanol plant, namely ethanol and corn oil, need not be transported great distances thereby giving significant savings. Nor is there a need for commercial sourcing of the alcohol or corn oil needed for the biodiesel fuel plant.

DETAILED DESCRIPTION OF THE PREFERRED EMBODIMENT

Figure 1:
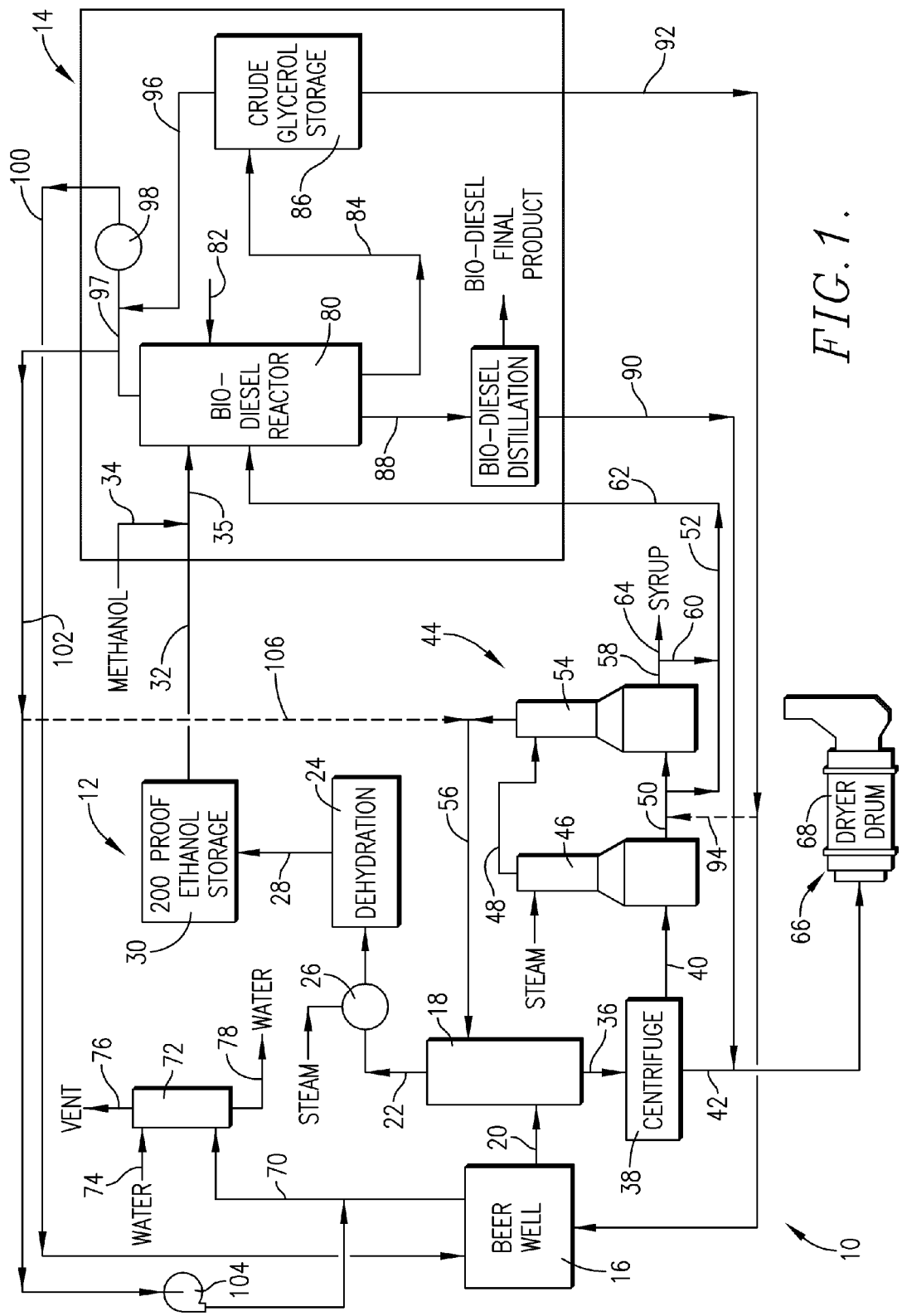
FIG. 1 is a schematic diagram of an integrated ethanol and biodiesel production facility in accordance with the invention, and illustrating several optional features.

Turning now to FIG. 1, an integrated ethanol and biodiesel production facility 10 is illustrated. The facility 10 broadly comprises an ethanol plant 12 and a biodiesel plant 14. As illustrated, the ethanol plant 12 and biodiesel plant 14 are co-located so that products and by-products of each facility can be readily shared, thereby reducing equipment and operating costs for the overall facility 10. As used herein, the term "by-product" refers not only to reaction products, but materials fed to a reaction vessel in excess that are later recovered from the reaction vessel and separated from the reaction products.

Ethanol plant 12 may be configured in a conventional manner, with the starting biomass material undergoing initial processing and fermentation to produce an ethanol-containing "beer." In the particular embodiment illustrated, the ethanol plant 12 utilizes a biomass material as the source of carbohydrates and sugars for the fermentation process. A plant or vegetable oil is an important by-product of the ethanol plant 12, inasmuch as this by-product forms the feedstock to the biodiesel plant 14, so that the biomass material should contain suitable amounts of plant oils. Exemplary biomass feed materials include corn, sorghum, and pearl millet. In the U.S., corn is the predominant feedstock for fuel ethanol production. Accordingly, the description set forth below is made with respect to corn and corn by-products. However, it should be understood that this description is exemplary only, and should not be taken as a limitation on the scope of the present invention.

The preparation and fermentation of corn feedstock within ethanol plant 12 may be carried out according to any number of methods known to those skilled in the art, and thus need not be fully described herein. In any case, following fermentation, the resultant ethanol-containing beer may be stored within a beer well 16 while it awaits further processing. Typically, the beer comprises from about 10-20% by volume ethanol, more preferably about 15% by volume ethanol. The beer also contains from about 5-20% by weight solids, more preferably about 10% by weight solids.

The beer is fed to distillation apparatus 18 via stream 20 for separation and recovery of the ethanol contained therein. Distillation apparatus 18, which may comprise one or more distillation columns, produces an overhead stream 22 primarily comprising ethanol and some water (e.g., from about 80-99% by volume ethanol, preferably from about 90-98% by volume ethanol, and most preferably about 95% by volume ethanol), with the balance of the stream primarily including water. In order to be suitable for use as fuel-grade ethanol, the remaining water needs to be removed from overhead stream 22. This water separation may be accomplished by means of a dehydration unit 24, which can be equipped with molecular sieve technology to achieve this separation. In certain embodiments, the molecular sieve comprises an alumino silicate material. In certain embodiments, stream 22 is condensed so that a portion can be refluxed back to apparatus 18, however, this need not always be the case. In those embodiments in which stream 22 was previously condensed, the stream should be vaporized before it is passed to dehydration unit 24. This vaporization can be accomplished by one or more heat exchangers 26 feed with steam supplied via a plant distribution header. A substantially pure ethanol stream 28 (i.e., greater than 99% by volume ethanol, or approximately 200 proof) exits dehydration unit 24 and is stored in a storage vessel 30 to await further processing.

As illustrated in FIG. 1, one of the feedstock inputs to the biodiesel plant 14 contains alcohol. This typically is the ethanol from line 32. However, if desired, methanol from line 34 may be used as the alcohol feedstock, either alone or mixed with the ethanol in line 32. Thus, the alcohol-containing feedstock 35 to plant 14 is either ethanol, methanol, or a mixture of methanol and ethanol.

The bottoms from distillation apparatus 18 comprise a whole stillage stream 36. Several products can be produced from whole stillage stream 36 including corn oil, a nutritive corn syrup, and dried distillers grains with solubles (DDGS). The whole stillage stream 36 may be separated by a centrifuge 38 into a thin stillage stream 40 and a cake stream 42. The thin stillage stream 40 generally comprises between about 5% to about 10% by weight solids, and more preferably about 7% by weight solids. The balance of the thin stillage comprises mainly water and corn oil. The thin stillage is concentrated within a multiple-effect evaporator 44. Steam from the steam distribution header is introduced into a first effect 46 in indirect heat exchange relationship with the thin stillage stream 40. Moisture is evaporated from the thin stillage and removed from first effect 46 as process steam stream 48. The concentrated stillage product is removed from first effect 46 via line 50 and a portion of the corn oil contained therein is separated as stream 52. The separation of the corn oil may be achieved through the use of a mechanical separation device (not shown), such as a decanter system (e.g., the TRICANTER from Flottweg Separation Technology, Germany), or a disc stack unit. The concentrated stillage product (minus the corn oil that was removed) is passed through a second effect 54 wherein steam from stream 48, through indirect heat exchange, causes a portion of the moisture contained within the concentrated stillage product to evaporate. This vapor is returned to distillation apparatus 18 via stream 56.

The stillage product now comprises a viscous syrup and is withdrawn from the second effect 54 via stream 58. Additional corn oil is removed from the viscous syrup in stream 58 by means of a secondary separation device (not shown), and this additional corn oil is directed via line 60 to stream 52. This forms a combined stream 62 which is directed to biodiesel plant 14 as a feedstock input thereto. The syrup having the oil removed therefrom is recovered as a product stream 64.

In an alternate embodiment of the present invention, the corn oil may be extracted prior to fermentation. For example, the corn oil may be extracted via pressing or solvent extraction prior to fermentation. In such case, the processing of the thin stillage occurs as mentioned above, with the exception of corn oil recovery.

The cake stream 42 from centrifuge 38 is conveyed toward drying apparatus 66 in which moisture is removed and DDGS produced. Drying apparatus 66 comprises one or more dryer drums 68 that are supplied by a hot air stream from a conventional fuel-fired heater (not shown).

The gaseous overhead from beer well 16 comprises carbon dioxide. This overhead is directed via line 70 to a $CO_2$ scrubber 72 having a water inlet line 74. In scrubber 72, the $CO_2$ is stripped and vented through vent line 76, and an underflow line 78 principally containing water, along with some alcohol (in certain embodiments, approximately 3% ethanol), is generated.

As previously described, there are two feedstock inputs to plant 14, namely alcohol feedstock 35 and corn oil stream 62. These feedstocks are directed to biodiesel reactor system 80 where the corn oil first undergoes an acid esterification reaction whereby the free fatty acids are converted to alkyl esters through the introduction of a strong acid (e.g., sulfuric acid) via line 82. The triglycerides are then subjected to base-catalyzed reaction in the presence of a strong base (e.g., KOH) and the alcohol feedstock 35, in order to form alkyl (methyl, ethyl and/or propyl) esters and glycerol. The ester reaction product is then directed to a wash/dry tank (not shown) forming a part of system 80, in which the esters are separated from the glycerol. In alternate embodiments, the washing and drying of the ester reaction product may be conducted within the same vessel where the transesterification reaction is conducted thereby reducing the capital costs associated with a separate wash/dry tank. The latter fraction, also containing excess alcohol used in the transesterification reactions, is directed via line 84 to a storage tank 86. The ester fraction is sent via line 88 to a biodiesel distillation column where the biodiesel final product is separated for use, and the distillation bottoms (principally comprising high boiling components and unreacted mono- and polyglycerides, e.g., di- and triglycerides) are sent via line 90 and are combined with the cake stream 42 prior to drying thereof. In certain preferred embodiments, the biodiesel final product is a fuel comprised of mono-alkyl esters of long chain fatty acids, commonly designated B100, and meeting the requirements of ASTM D 6751, incorporated by reference herein.

A liquid fraction of the alcohol/glycerol mixture within storage tank 86 is directed via line 92 to beer well 16, as shown, where it will then be sent to distillation apparatus 18. In alternate embodiments, some or all of the contents of line 92 may be directed through line 94 to the concentrated stillage line 50 for mixing therein, prior to entering the second effect 54. In the effect 54, the alcohol is vaporized along with water, and this water/alcohol mixture is returned via stream 56 to distillation apparatus 18.

The gaseous alcohol-containing overheads from reactor system 80 and tank 86 are directed through lines 96 and 97 to vent condenser 98. These alcohol-containing overheads may also comprise water vapor that is carried along with the alcohol. The resultant condensed alcohol liquid fraction from condenser 98 is then sent through line 100 to beer well 16 for further processing in plant 12. In an alternative embodiment, some or all of the gaseous overheads in lines 96 and 97 are directed through a line 102 equipped with a blower 104 for mixing with the beer well overhead 70 prior to entrance into scrubber 72. In a still further alternate embodiment, some of all of the contents of line 102 may be directed via line 106 for mixture with the contents of stream 56 directed from evaporator 54 to distillation apparatus 18.

In conventional biodiesel plants, the crude glycerol directed to tank 86 contains methanol produced in the biodiesel reaction, and this methanol must be separated before the glycerol is disposed of or used as a commercial product. This requires additional separation equipment, which represents a significant capital expense, and moreover the glycerol/methanol separation requires an energy input. In the present invention, however, use is made of the existing separation equipment present in the ethanol plant to further process the glycerol/methanol mixture, namely distillation apparatus 18, second effect 54, associated recovery lines 58, 60, and 62, overhead vent line 96, condenser 98, and recovery line 100. As such, capital equipment costs are reduced and very little additional energy is required.

Figure 2:
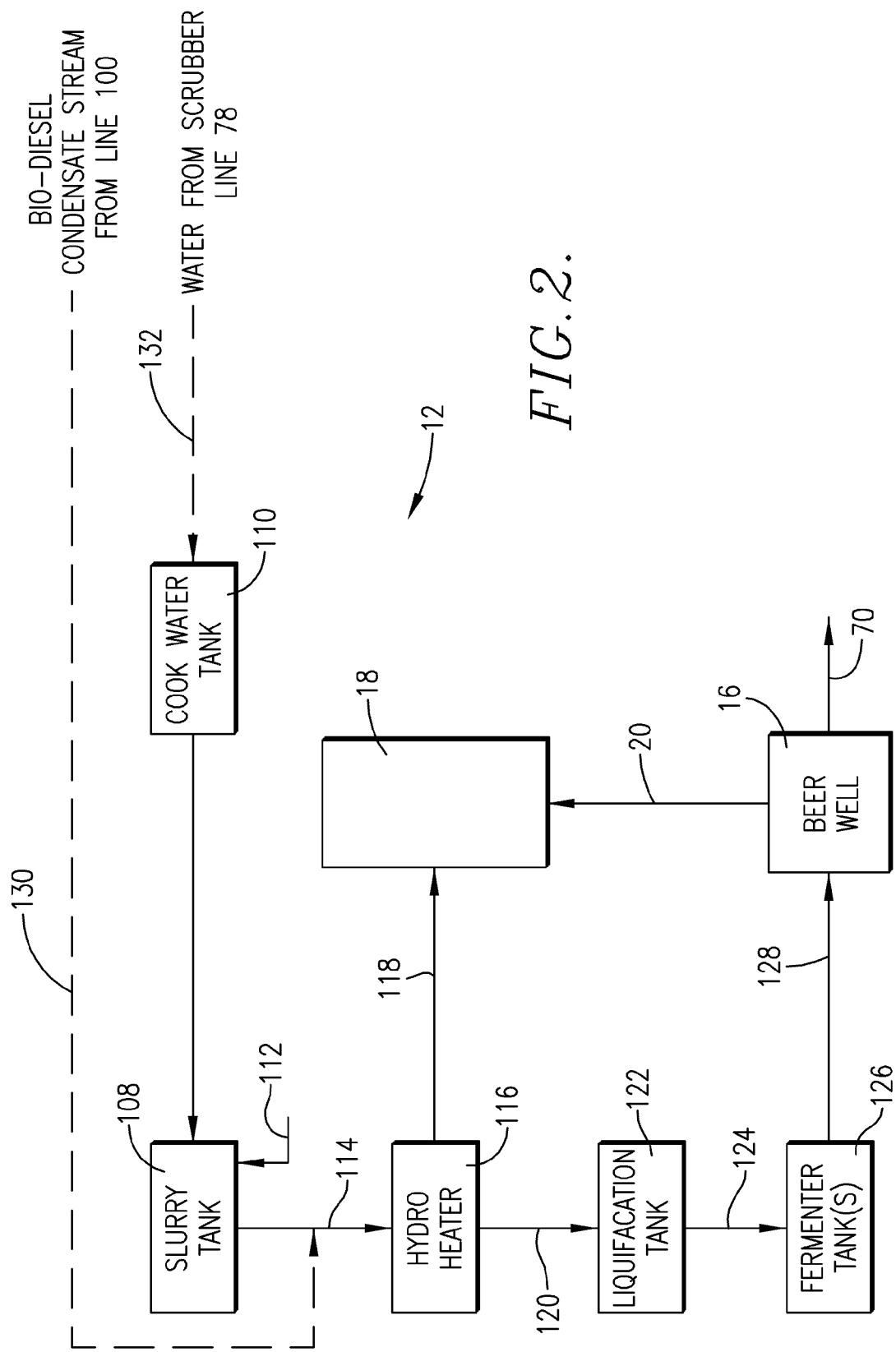
FIG. 2 is a schematic diagram of another embodiment of the invention, illustrating a further optional feature for the combined production facility.

FIG. 2 illustrates a still further embodiment of the invention, wherein the condensate stream from line 100 and the water from scrubber line 78 are integrated into the plant 12 in a different manner. Although not shown in FIG. 1, the plant 12 additionally includes a number of conventional components upstream of beer well 16 and distillation apparatus 18. Specifically, a slurry tank 108 is provided, which is used to create the initial corn/water slurry, using water from a cook water tank 110. The slurry within tank 108 is also steam-heated via line 112. The heated slurry is then passed through line 114 to a hydroheater 116, wherein the slurry is further steam-heated. A fraction of the heated slurry is then fed to apparatus 18 via line 118, with the remainder being directed through line 120 to liquifaction tank 122. The output from tank 122 is directed through line 124 to fermenter tank(s) 126 to yield the ethanol-containing beer sent via line 128 to beer well 16.

In the FIG. 2 embodiment, the condensate stream from line 100 is directed through line 130 for mixture with the output from slurry tank 108 in line 114. Furthermore, the water from scrubber line 78 is fed through line 132 to cook water tank 110.

It is understood that the various integrations between biodiesel plant 14 and ethanol plant 12 described above may be carried out jointly, individually, or in any combination thereof, as the requirements of any given facility 10 dictate. However, use of the alcohol and corn oil outputs from the ethanol plant 12, coupled with the use of the biodiesel fuel plant by-products, is preferred and is believed to the give maximum efficiency advantages.

The invention claimed is:

1. An integrated facility for the co-production of ethanol and biodiesel fuel using corn as a feedstock, comprising:
   an ethanol plant operable to produce ethanol and a corn oil product from an ethanol-containing beer;
   a biodiesel plant comprising a reactor assembly operably coupled with said ethanol plant to receive at least some corn oil product from the said ethanol plant, and to react said corn oil with alcohol to produce said biodiesel fuel and one or more by-products selected from the group consisting of methanol, ethanol, glycerol, and combinations thereof; and structure for transferring at least one of said by-products to said ethanol plant for distillation within a distillation apparatus or mixing with a stillage stream of said distillation apparatus undergoing concentration within said ethanol plant, wherein said ethanol-containing beer is contained within a beer well, said beer well generating a gaseous overhead comprising $CO_2$, at least one of said by-products being directed in gaseous form from said biodiesel plant to said ethanol plant for combination with said beer well overhead.

2. The facility of claim 1, wherein said reactor assembly is operable to generate a supply of liquid crude glycerol, at least some of said liquid crude glycerol being sent from said biodiesel plant to said ethanol plant for mixture with said beer.

3. The facility of claim 1, wherein said ethanol plant includes apparatus for creating a heated corn/water slurry, said beer well generating a gaseous overhead comprising $CO_2$, said ethanol plant including a $CO_2$ scrubber operable to receive said beer well overhead and to create a water stream, at least part of said water stream from said $CO_2$ scrubber is used as a part of said corn/water slurry.

4. An integrated facility for the co-production of ethanol and biodiesel fuel using corn as a feedstock, comprising:
   an ethanol plant operable to produce ethanol and a corn oil product from an ethanol-containing beer;
   a biodiesel plant comprising a reactor assembly operably coupled with said ethanol plant to receive at least some corn oil product from said ethanol plant, and to react said corn oil with alcohol to produce said biodiesel fuel and one or more by-products selected from the group consisting of methanol, ethanol, glycerol, and combinations thereof; and
   structure for transferring at least one of said by-products to said ethanol plant for distillation within a distillation apparatus or mixing with a stillage stream of said distillation apparatus undergoing concentration within said ethanol plant,
   wherein said distillation apparatus is operable to create whole stillage, said ethanol plant further comprises a separation assembly operable to generate a thin stillage stream from said whole stillage, and an evaporator apparatus operable to separate said corn oil product from said thin stillage stream, and to generate a steam overhead, at least one of said by-product from said biodiesel plant being mixed in gaseous form with said steam overhead.

5. The facility of claim 4, wherein said evaporator apparatus comprises a multiple-effect evaporator including first and second effects, said glycerol supply being sent from said biodiesel plant to said ethanol plant for mixture with a concentrated thin stillage product from said first effect.

6. An integrated facility for the co-production of ethanol and biodiesel fuel using corn as a feedstock, comprising:
   an ethanol plant operable to produce ethanol and a corn oil product from an ethanol-containing beer;
   a biodiesel plant comprising a reactor assembly operably coupled with said ethanol plant to receive at least some corn oil product from said ethanol plant, and to react said corn oil with alcohol to produce said biodiesel fuel and one or more by-products selected from the group consisting of methanol, ethanol, glycerol, and combinations thereof; and
   structure for transferring at least one of said by-products to said ethanol plant for distillation within a distillation apparatus or mixing with a stillage stream of said distillation apparatus undergoing concentration within said ethanol plant,
   wherein said ethanol plant includes apparatus for creating a heated corn/water slurry and said biodiesel plant includes apparatus operable to condense at least one of said by-products to generate a condensed by-product containing said ethanol or said methanol, said condensed by-product being sent-from said biodiesel plant to said ethanol plant for mixture with said heated corn/water slurry.

\* \* \* \* \*